United States Patent
Bottai

(10) Patent No.: US 11,504,307 B2
(45) Date of Patent: Nov. 22, 2022

(54) TOPICAL PRODUCTS WITH A BIPHASIC SYSTEM

(71) Applicant: CMED AESTHETICS s.r.l., Pisa (IT)

(72) Inventor: Elena Bottai, Pisa (IT)

(73) Assignee: CMED AESTHETICS S.R.L., Pisa (IT)

(*) Notice: Subject to any disclaimer, the term of this patent is extended or adjusted under 35 U.S.C. 154(b) by 0 days.

(21) Appl. No.: 16/644,975

(22) PCT Filed: Sep. 18, 2018

(86) PCT No.: PCT/IB2018/057131
§ 371 (c)(1),
(2) Date: Mar. 6, 2020

(87) PCT Pub. No.: WO2019/058249
PCT Pub. Date: Mar. 28, 2019

(65) Prior Publication Data
US 2020/0276090 A1    Sep. 3, 2020

(30) Foreign Application Priority Data
Sep. 19, 2017 (IT) .................. 102017000104536

(51) Int. Cl.
| | |
|---|---|
| *A61K 8/03* | (2006.01) |
| *A61K 8/362* | (2006.01) |
| *A61K 8/365* | (2006.01) |
| *A61K 8/368* | (2006.01) |
| *A61K 8/37* | (2006.01) |
| *A61K 8/44* | (2006.01) |
| *A61K 8/67* | (2006.01) |
| *A61K 8/92* | (2006.01) |
| *A61Q 19/00* | (2006.01) |
| *A61K 8/60* | (2006.01) |

(52) U.S. Cl.
CPC .............. *A61K 8/03* (2013.01); *A61K 8/362* (2013.01); *A61K 8/365* (2013.01); *A61K 8/368* (2013.01); *A61K 8/37* (2013.01); *A61K 8/44* (2013.01); *A61K 8/60* (2013.01); *A61K 8/673* (2013.01); *A61K 8/676* (2013.01); *A61K 8/92* (2013.01); *A61Q 19/00* (2013.01); *A61K 2800/28* (2013.01)

(58) Field of Classification Search
None
See application file for complete search history.

(56) References Cited

U.S. PATENT DOCUMENTS

| | | | |
|---|---|---|---|
| 4,569,839 A * | 2/1986 | Grollier | A61K 8/9789 424/74 |
| 5,965,145 A | 10/1999 | Marion et al. | |
| 2002/0192253 A1* | 12/2002 | Itoh | A61K 31/197 424/401 |
| 2004/0029829 A1* | 2/2004 | Miyazaki | A61K 8/9789 514/54 |
| 2005/0004509 A1* | 1/2005 | Sun | A61N 1/0428 604/20 |
| 2006/0134059 A1* | 6/2006 | Dryer | A61P 17/00 424/74 |
| 2009/0029928 A1* | 1/2009 | Aubrun-Sonneville | A61K 8/368 514/27 |
| 2009/0047226 A1* | 2/2009 | Teckenbrock | A61K 8/732 424/59 |
| 2009/0117068 A1 | 5/2009 | Ellis et al. | |
| 2014/0037561 A1 | 2/2014 | Kulseza et al. | |
| 2014/0328952 A1* | 11/2014 | Flavin | A61K 8/9794 424/728 |
| 2016/0250130 A1* | 9/2016 | Mas | A61K 8/41 424/637 |
| 2017/0296613 A1* | 10/2017 | Hendriks | A61K 31/194 |

FOREIGN PATENT DOCUMENTS

| | | | |
|---|---|---|---|
| EP | 1374831 | 1/2004 | |
| JP | 2000186036 | 7/2000 | |
| WO | WO-0069403 A1 * | 11/2000 | .......... A61K 31/195 |
| WO | 2007042824 | 4/2007 | |
| WO | WO-2008139182 A2 * | 11/2008 | .......... A61K 8/9789 |

OTHER PUBLICATIONS

Bruce et al. Journal of Drugs in Dermatology 2016 15(9):1145-1150 (Year: 2016).*
Ball Journal of Chemical Education 2007 84(10):1643-1646 (Year: 2007).*
Mohammed et al. Australian Journal of Basic and Applied Sciences 2010 4(4): 552-556 (Year: 2010).*
International Search Report.
Database GNPD [online] Mintel; Feb. 1, 2014, 40% Triple Acid Peel, XP002780048, Database accession No. 22769907.

* cited by examiner

*Primary Examiner* — Melissa S Mercier
*Assistant Examiner* — Caralynne E Helm
(74) *Attorney, Agent, or Firm* — Jacobson Holman PLLC

(57) ABSTRACT

A biphasic topical product comprising a hydrophilic phase and a lipophilic phase floating on said hydrophilic phase. A method for preparing biphasic topical products.

15 Claims, 1 Drawing Sheet

TOPICAL PRODUCTS WITH A BIPHASIC SYSTEM

FIELD OF THE INVENTION

The present invention relates to topical products with a biphasic system, as well as to a method for preparing the same.

BACKGROUND ART

In the medical and dermocosmetic field, it is common practice to use acidic substances to exploit the exfoliating activity in skin treatments. These treatments are called chemical peels, from the verb "to peel". Their main action is to rejuvenate the skin and, as a result, promote skin renewal by promoting the removal of the most superficial skin layers through chemical exfoliation. This type of treatment is capable of acting on the skin through the action of different mechanisms, including the stimulation of cellular regeneration (turnover), thus eliminating and exfoliating the dead cells of the horny layer.

Subsequently, the damaged or otherwise degenerated cells are eliminated, which in turn are replaced by epidermal cells. Among the most used substances for chemical peels, there are: trichloroacetic acid, glycolic acid, resorcinol, salicylic acid, pyruvic acid, phenol, mandelic acid, lactic acid, retinoic acid, kojic acid, citric acid, pyruvic acid etc. The action of these treatments depends on the type of acid used, the concentration and chemical stability thereof and also the area of application. Trichloroacetic acid is one of the most widely used substances owing to its marked exfoliating properties.

At the chemical level, it is a carboxylic acid, which at room temperature appears as a crystalline colorless solid with a pungent, strongly hygroscopic and highly oxidizable odor. Trichloroacetic acid has a structure comparable to that of acetic acid to which the three hydrogen atoms have been substituted with three chlorine atoms. This substitution shifts the electronic charge of the "alpha" carbon towards the chlorine atoms, thus determining a condition of partial electron-deficiency on the above-mentioned carbon, which in turn attracts the electronic charge of the adjacent carbon and therefore of the oxygen, which will tend to divide the proton more significantly if introduced into an aqueous environment, owing to the marked delocalization of the negative charge.

The particular electronic organization of the molecule, due to the high negative potential generated by the three chlorine atoms on the carbon in "beta" shifts the electronic balance towards the chlorine atoms and makes the molecule less stable and oxidizable, thus facilitating the cleavage between carbon in alpha and beta, resulting in the formation of formic acid and chloroform, harmful substances, highly irritating and allergenic to the dermis.

The oxidation of trichloroacetic acid is known in the medical field, as it involves the browning of the products containing the same, normally used in the form of monophasic hydrogels, with a relative cleavage of the trichloroacetic acid molecule. The browning of the compound, in addition to the loss of activity of the product, also entails a very significant loss of safety of the product containing trichloroacetic acid, since the latter will no longer contain the trichloroacetic acid as such, but a mixture of trichloroacetic acid, chloroform and formic acid. The mixture will tend to be composed of the latter as the oxidative process completes until the total trichloroacetic acid contained in the product is split.

WO2007/042824A1 describes a composition comprising trichloroacetic acid, alpha-, beta- and polyhydroxy acids, vitamins, amino acids. Said composition is an emulsion with an oil phase consisting of polysiloxanes, silicones, mineral oils or essential oils.

US2009/0117068 describes a solid composition applicable to a razor. Said composition comprises hydroxy acids, polyhydroxy acids, trichloroacetic acid.

Disadvantageously, said cosmetic compositions do not provide a protection for the trichloroacetic acid which, upon contact with oxygen, can oxidize and modify its nature.

Another drawback is due to the fact that there is not a system which allows the use of the topical composition in complete safety even after opening a package which contains the same.

US2014/037561 describes compositions comprising trichloroacetic acid, which is stabilized with a mixture of chemical stabilizing agents in ratios from 0.1:1 to 5:1. In Example 5, it is stated that under the same conditions, after 90 days, while the TCA in aqueous solution alone degrades by 12.6%, when it is in the presence of a low percentage of stabilizing agents, it degrades on average by 4-5%, and when it is in the presence of a high percentage of stabilizing agents, it degrades on average by 2-3%. Therefore, the teaching is to increase the amount of chemical stabilizing agents with respect to the TCA, however without providing information about the trend of this degradation over 90 days, and certainly without having considered the impact on the tolerability of the composition on the skin.

The object of the present invention is therefore to obtain products for medical use, in particular for topical use, capable of maintaining constant over time the properties of all the components present in the products.

Another object is to obtain topical products capable of preserving the nature of trichloroacetic acid.

SUMMARY OF THE INVENTION

According to the invention, these objects are achieved by a biphasic topical product as described in claim 1.

In another aspect, the present invention relates to a method for preparing topical products capable of preserving the nature of trichloroacetic acid and preventing oxidation thereof.

BRIEF DESCRIPTION OF THE DRAWING

The characteristics and advantages of the present invention will become more apparent from the following detailed description, the embodiments shown by way of non-limiting examples, and the accompanying drawing, wherein:

FIG. 1 shows the biphasic product of Example 1.

DETAILED DESCRIPTION OF THE INVENTION

The invention therefore relates to a biphasic topical product comprising a mixture of hydroxy acids, trichloroacetic acid and bioactive substances with non-exfoliating activity, wherein two phases are present, a hydrophilic phase and a lipophilic phase. Said lipophilic phase floats above the hydrophilic phase, so that the latter does not come into direct contact with the oxygen present in the atmosphere. In fact, as will be clear from the following Examples and as clearly illustrated in FIG. 1, the biphasic product of the present invention has and maintains a clear-cut separation surface between the two phases immiscible with each other, since the product is free of emulsifying surfactants. In this sense, it has surprisingly been found that the lipophilic phase overlying the hydrophilic phase, wherein trichloroacetic acid (or TCA) is present, creates a physical barrier which isolates the hydrophilic phase, thus preventing the contact with the air and therefore, as said, with oxygen causing the oxidation of TCA. This allows overcoming the drawbacks associated with the emulsions of the prior art, which instead left the phase containing TCA inevitably exposed to air.

It follows that TCA, as well as the entire hydrophilic phase as a whole, is conserved for very long periods of time, even for a few years, without significant variations and above all without the use of stabilizers or chemical preservatives.

It should in fact be noted that reducing the use of stabilizers and chemical preservatives as much as possible ensures products which are much more natural and tolerable from the dermatological point of view. However, on the other hand, the absence of stabilizers and chemical preservatives makes natural products themselves more delicate than "chemical" ones, and more subject to degradation.

The solution provided by the present invention is therefore particularly advantageous in that it allows eliminating the use of stabilizers and chemical preservatives without compromising the stability of the product, on the contrary obtaining a long and constant preservation capacity over time. The biphasic product of the present invention is therefore both highly tolerable by the skin, even in the case of subjects exposed to allergies, and extremely stable, as well as visually pleasing and commercially attractive.

The biphasic topical product of the invention therefore comprises a mixture of hydroxy acids, trichloroacetic acid and bioactive substances with non-exfoliating activity, wherein said topical product comprises a hydrophilic phase and a lipophilic phase, the biphasic topical product being free of emulsifying surfactants, and said bioactive substances with non-exfoliating activity comprise a mixture of vitamins and amino acids.

Preferably, the biphasic topical product is also free of stabilizers and preservatives.

This mixture of hydroxy acids, trichloroacetic acid and bioactive substances is present in the hydrophilic phase.

Said hydroxy acids may be alpha-hydroxy acids, beta-hydroxy acids, or polyhydroxy acids.

The alpha hydroxy acids are for example selected from tartaric acid, citric acid, glycolic acid, lactic acid, malic acid; the beta hydroxy acids are for example selected from hydroxybutyric acid and salicylic acid; the polyhydroxy acids are for example selected from lactobionic acid and gluconolactone.

The hydrophilic phase preferably comprises tartaric acid, citric acid, salicylic acid and lactobionic acid.

Tartaric acid is present in a final concentration of 2% to 15%, preferably 3% to 12%, even more preferably 4% to 10%. For the purposes of the present invention, "%" means "% by weight" based on the weight of the phase wherein the ingredient is present.

Citric acid is present in a final concentration by weight of 0.3% to 5%, preferably 0.4% to 4%, even more preferably 0.5% to 3%.

Salicylic acid is present in a final concentration by weight of 0.5% to 14%, preferably 0.75% to 12%, even more preferably 1% to 10%.

Lactobionic acid is present in a final concentration by weight of 3% to 10%, preferably 4% to 13%, even more preferably 5% to 11%.

Trichloroacetic acid has a final concentration by weight of 5% to 60%, preferably 7% to 55%, even more preferably 9% to 50%.

The amino acids present in the hydrophilic phase are for example glycine, proline, hydroxy-proline and arginine. Said amino acids have a final concentration by weight of 0.01% to 12%, preferably 0.02% to 10%, even more preferably 0.03% to 10%.

The vitamins present in the hydrophilic phase have a final concentration by weight of 0.05% to 2%, preferably 0.06% to 1.5%, even more preferably 0.07% to 1%.

The vitamins present in the hydrophilic phase are riboflavin (Vitamin B2) and Vitamin C.

The hydrophilic phase also comprises gamma-aminobutyric acid (GABA) or dimethylaminoethanol with a contracturant and muscle relaxant action.

GABA is present in a final concentration of 1% to 10%, preferably 2% to 8%, even more preferably 3% to 7%.

Dimethylaminoethanol is present in a final concentration by weight of between 0.1% and 1%, preferably between 0.2% and 0.8%, even more preferably between 0.3% and 0.7%.

The hydrophilic phase may further comprise additives, pH adjusters, wetting agents, rheological modifiers, such as viscosizing and gelling agents. For example, it may comprise cationic polymers, cellulose derivatives of natural and semisynthetic extraction, silica and derivatives, EDTA, potassium hydrogen phosphate, and sodium hydroxide.

Said hydrophilic phase further comprises water.

The lipophilic phase of the topical product comprises wetting and emollient agents and a heterogeneous mixture of heavy oils and saturated paraffinic hydrocarbons, such as petrolatum oil.

The emollient and wetting agent may be selected from isopropyl myristate and isopropyl palmitate, preferably isopropyl myristate, in a final concentration of 30% to 75%, preferably 40% to 70%.

Petrolatum oil is present in a final concentration of 20% to 50%, preferably 25% to 45%, even more preferably 30% to 40%.

In preferred embodiments, the lipophilic phase comprises petrolatum oil, isopropyl myristate, squalane, or a mixture thereof, more preferably a mixture thereof.

The biphasic topical product of the present invention may be prepared by methods which comprise the mixing of the individual components of each phase, and then the subsequent addition of the lipophilic phase to the hydrophilic phase. However, a method dedicated in particular to the preparation of the preferred embodiments of the product of the invention has been developed.

A second aspect of the present invention therefore comprises a method for preparing a product for topical use, preferably for external topical use.

Said method comprises the following steps:
providing a certain quantity of wetting agents and water;
preparing a mixture of salicylic acid, citric acid, tartaric acid, lactobionic acid and trichloroacetic acid;
solubilizing the remaining components;
preparing a solution of sodium hydroxide to adjust the pH of the above-mentioned mixture;
proceeding with pH adjustment;
providing adequate quantities of lipophilic components, which should be mixed together;

the two phases (portioned/added) form at the time of packaging when the two phases are added at successive times, the hydrophilic phase first and then the lipophilic phase.

Said method preferably comprises the following steps:
providing a certain quantity of wetting agents and water;
preparing the mixture by adding salicylic acid first, then the remaining acids in order from the least concentrated to the most concentrated: citric acid, tartaric acid, lactobionic acid and trichloroacetic acid;
preparing a solution of sodium hydroxide to adjust the pH of the above-mentioned mixture;
adjusting the pH up to a value of 1 to 2.5, with a tolerance of 0.5;
solubilizing the remaining components in order from the least concentrated to the most concentrated;
providing adequate quantities of lipophilic components, which should be mixed together;
the two phases form at the time of packaging when the two phases are added at successive times, the hydrophilic phase first and then the lipophilic phase.

As mentioned, the main function of the lipophilic phase is to protect the trichloroacetic acid from oxidation, acting as a mechanical barrier against the oxygen present inside the final bottle where the product is portioned. The oxygen in contact with the preparation in the closed bottle would activate the oxidation process with browning (cleavage of the trichloroacetic acid, per se it does not darken, but splits) of the trichloroacetic acid and the relative conversion of the latter into degradation products which are harmful, highly irritating and allergenic to the dermis such as chloroform and formic acid.

For this reason, in the present invention, the lipophilic phase acts as a protection mechanism, thus avoiding contact between the hydrophilic phase, containing the trichloroacetic acid, and the oxygen contained in the bottle even after stirring and mixing between the hydrophilic and lipophilic phase, as a microfilm of lipophilic phase remains constantly above the hydrophilic phase due to density difference and thus permanently protecting the compound from contact with oxygen, and thus preventing the oxidation of trichloroacetic acid, avoiding the conversion thereof into harmful substances for the skin.

The two phases may be of two different colors, which choice makes the product even more appealing from the commercial point of view and for the overall pleasantness, for example, yellow for the hydrophilic phase and blue for the lipophilic phase.

The second function of the lipophilic phase in addition to that of protecting trichloroacetic acid is to perform a filming, emollient and moisturizing activity on the skin, owing to its composition preferably obtained with: isopropyl-myristate, wetting and moisturizing with natural derivation from nutmeg; squalane with protective function of the skin, due to the ability to regenerate the lipid film which prevents aggression by external agents, and moisturizing, reducing the evaporation of water from the deeper epidermal layers and petrolatum oil which creates a protective film (occlusive film), capable of decreasing trans-epidermal water loss.

The hydrophilic phase is characterized not only by trichloroacetic acid, but also preferably by an innovative mixture of alpha (tartaric acid, citric acid), beta (salicylic acid) and poly (lactobionic acid) hydroxy acids rich in hydroxyls, selected and dosed advantageously in the present invention, and which perform an additional direct hydration function in addition to the already known exfoliating one. Moreover, the synergy of trichloroacetic acid and salicylic acid, known as keratolytics, allows the penetration of the pool of amino acids, vitamins and bioactive substances present in the preparation. The amino acids present in the preparation, preferably glycine, proline, hydroxyproline, arginine, lysine or mixtures thereof, play a stimulating action in the synthesis of collagen, being natural constituents, and activate capillary microcirculation by favoring the biostimulation processes.

It has been possible to introduce amino acids, for the first time in this type of treatment, advantageously exploiting the isoelectric equilibrium of the latter in acidic solution. Vitamin C acts as a catalyst for the formation of new collagen in synergy with amino acids. The hydrophilic phase also contains gamma amino butyric acid or dimethylaminoethanol with a decontracting and muscle relaxant action.

The present invention finally relates to the topical, preferably external topical use of the biphasic product in the dermatological and dermocosmetic treatment of the skin, in particular in skin peeling treatments.

It should be understood that all the possible combinations of the preferred aspects of the components of the two-phase product, its preparation and their uses are deemed to be described and therefore similarly preferred.

It should also be understood that all aspects identified as preferred and advantageous for the biphasic product and its components should be deemed as similarly preferred and advantageous also for the preparation and uses of the biphasic product itself.

The following examples are non-limiting embodiments of the present invention.

EXAMPLES

Example 1

A biphasic topical product according to the present invention was prepared, having the following composition:

| Trade name | INCI Name | wt % |
| --- | --- | --- |
| Hydrophilic phase | | |
| EDTA | Disodium EDTA | 0.01 |
| RIBOFLAVIN | Riboflavin | 0.1 |
| SODIUM ASCORBATE | Sodium ascorbate | 2 |
| GLYCINE | Glycine | 0.1 |
| PROLINE | Proline | 0.1 |
| HYDROXYPROLINE | Hydroxyproline | 0.1 |
| SALICYLIC ACID | Salicylic acid | 3 |
| POLYQUATERNIUM 10 | Polyquaternium-10 | 2.5 |
| POTASSIUM HYDROGEN PHOSPHATE | Potassium phosphate dibasic | 1.5 |
| CITRIC ACID | Citric acid | 1 |
| AMINOBUTYRIC ACID | Aminobutyric acid | 1 |
| TARTARIC ACID | Tartaric acid | 5 |
| LACTOBIONIC ACID | Lactobionic acid | 5 |
| ARGININE | Arginine | 5 |
| TRICHLOROACETIC ACID | Trichloroacetic acid | 35 |
| SODIUM HYDROXIDE | Sodium hydroxide | 4 |
| HYDROPHILIC YELLOW STAIN | CI 19140 | 0.001 |
| WATER | AQUA | Balance to 100% |
| Lipophilic phase | | |
| ISOPROPYL MYRISTATE | Isopropyl myristate | 40 |
| PETROLATUM | Petrolatum | 39.999 |
| SQUALANE | Squalane | 20 |
| LIPOPHILIC BLUE STAIN | CI 61565 | 0.001 |

The resulting biphasic topical product is shown in FIG. 1, where it is clear that the underlying hydrophilic phase and the overlying lipophilic phase are evidently distinct from each other by a continuous separation surface.

Example 2

A biphasic topical product according to the present invention was prepared, having the following composition:

| Trade name | INCI Name | % by weight |
|---|---|---|
| Hydrophilic phase | | |
| EDTA | Disodium EDTA | 0.01 |
| RIBOFLAVIN | Riboflavin | 0.1 |
| SODIUM ASCORBATE | Sodium ascorbate | 2 |
| GLYCINE | Glycine | 0.1 |
| PROLINE | Proline | 0.1 |
| HYDROXYPROLINE | Hydroxyproline | 0.1 |
| SALICYLIC ACID | Salicylic acid | 3 |
| POLYQUATERNIUM 10 | Polyquaternium-10 | 2.5 |
| POTASSIUM HYDROGEN PHOSPHATE | Potassium phosphate dibasic | 1.5 |
| CITRIC ACID | Citric acid | 1 |
| AMINOBUTYRIC ACID | Aminobutyric acid | 1 |
| TARTARIC ACID | Tartaric acid | 5 |
| LACTOBIONIC ACID | Lactobionic acid | 5 |
| ARGININE | Arginine | 5 |
| TRICHLOROACETIC ACID | Trichloroacetic acid | 50 |
| SODIUM HYDROXIDE | Sodium hydroxide | 5.5 |
| HYDROPHILIC YELLOW STAIN | CI 19140 | 0.001 |
| WATER | AQUA | Balance to 100% |
| Lipophilic phase | | |
| ISOPROPYL MYRISTATE | Isopropyl myristate | 40 |
| PETROLATUM | Petrolatum | 39.999 |
| SQUALANE | Squalane | 20 |
| LIPOPHILIC BLUE STAIN | CI 61565 | 0.001 |

Example 3

A biphasic topical product according to the present invention was prepared, having the following composition:

| Ingredient | % m/v |
|---|---|
| Hydrophilic phase | |
| Trichloroacetic acid | 50 |
| Sodium hydroxide | 5.6 |
| Arginine | 4.17 |
| Lactobionic acid | 4.17 |
| Tartaric acid | 4.17 |
| Polyquaternium-10 | 2.08 |
| Salicylic acid | 1.67 |
| Sodium ascorbate | 1.67 |
| Potassium phosphate dibasic | 1.67 |
| Aminobutyric acid | 0.83 |
| Citric acid | 0.83 |
| Riboflavin | 0.01 |
| Hydroxyproline | 0.01 |
| Proline | 0.01 |
| Glycine | 0.01 |
| Disodium EDTA | 0.01 |
| CI 19140 | 0.001 |
| Water | 6.418 |
| Lipophilic phase | |
| Isopropyl myristate | 6.67 |
| Petrolatum | 6.67 |
| Squalane | 3.33 |
| CI 61565 | 0.001 |

Example 4

Evaluation of Stability
The product obtained in Example 3 was subjected to a test to verify its stability over time.
Materials and Methods
Thermostats:
MEMMERT HPP260—Memmert GmbH+Co.KG
Uncontrolled room temperature (° C.): 5°<T<25°
Controlled temperature (° C.): 20°
Controlled temperature (° C.): 25°
pH Meter:
pH meter Basic 20—CRISON INSTRUMENT, SA
Viscosimeter:
BROOKFIELD DV2T
Microbiological Analysis:
Seeding by Plate Inclusion:
AEROBIC MESOPHILIC BACTERIAL COUNT CFU/G method according to UNI EN ISO 21149: 20170 (briefly "CBT")
Parameters Evaluated
Time Correspondence:
12 weeks accelerated=1 year
24 weeks accelerated=2 years

| | | Storage conditions and frequency of analysis |  |
|---|---|---|---|
| | Specifications | 5° < T < 25°/60% ± 5% (Weeks) | |
| Parameter | Reference | 12 weeks | 24 weeks |
| Appearance, color, smell | Compliant with std. | Blue-Yellow compliant | Blue-Yellow compliant |
| pH | 1.5 ± 0.5 | 1.51 | 1.53 |
| Viscosity | 1000-2000 SP 6-20 RPM | 1546 | 1534 |
| CBT | <100 cfu/g | <100 cfu/g | <100 cfu/g |

| | | Storage conditions and frequency of analysis |  |
|---|---|---|---|
| | Specifications | T 20° ± 2/60% ± 5% (Weeks) | |
| Parameter | Reference | 12 weeks | 24 weeks |
| Appearance, color, smell | Compliant with std. | Blue-Yellow compliant | Blue-Yellow compliant |
| pH | 1.5 ± 0.5 | 1.52 | 1.56 |
| Viscosity | 1000-2000 SP 6-20 RPM | 1541 | 1552 |
| CBT | <100 cfu/g | <100 cfu/g | <100 cfu/g |

| | | Applicable storage conditions and frequency of analysis |  |
|---|---|---|---|
| | Specifications | T 25° ± 2/60% ± 5% (Weeks) | |
| Parameter | Reference | 12 weeks | 24 weeks |
| Appearance, color, smell | Compliant with std. | Blue-Yellow compliant | Blue-Yellow compliant |
| pH | 1.5 ± 0.5 | 1.53 | 1.58 |
| Viscosity | 1000-2000 SP 6-20 RPM | 1539 | 1545 |
| CBT | <100 cfu/g | <100 cfu/g | <100 cfu/g |

The above results clearly demonstrate the high stability of the product according to the invention, even under conditions of accelerated aging, for considerably prolonged periods of time, i.e. up to 2 years, without significant variations.

The invention claimed is:

1. A biphasic topical product comprising a mixture of hydroxy acids, trichloroacetic acid and bioactive substances with non-exfoliating activity, wherein the biphasic topical product comprises a hydrophilic phase and a lipophilic phase floating on the hydrophilic phase, the bioactive substances with non-exfoliating activity comprising a mixture of vitamins and amino acids, wherein the hydrophilic phase has a pH between 1 and 2.5 with a tolerance of 0.5 and comprises: tartaric acid at a final concentration by weight of 2% to 15%, citric acid at a final concentration by weight of 0.3% to 5%, salicylic acid at a final concentration by weight of 0.5% to 14%, lactobionic acid at a final concentration by weight of 3% to 13%, and trichloroacetic acid at a final concentration by weight of 5% to 60%, based on the weight of the hydrophilic phase, and wherein the lipophilic phase further comprises at least one wetting and emollient agent selected from isopropyl-myristate and isopropyl-palmitate, and petrolatum oil.

2. The topical product according to claim 1, wherein the hydrophilic phase further comprises gamma-amino-butyric acid (GABA) or dimethylaminoethanol.

3. The topical product according to claim 2, wherein the GABA is present at a final concentration by weight of 1% to 10%, or dimethylaminoethanol is present at a final concentration by weight of 0.1% to 1%, all final concentrations based on the weight of the hydrophilic phase.

4. The topical product according to claim 3, wherein the GABA is present at a final concentration by weight of 2% to 8%, or dimethylaminoethanol is present at a final concentration by weight of 0.2% to 0.8%, all final concentrations based on the weight of the hydrophilic phase.

5. The topical product according to claim 4, wherein the GABA is present at a final concentration by weight of 3% to 7%, or dimethylaminoethanol is present at a final concentration by weight of 0.3% to 0.7%, all final concentrations based on the weight of the hydrophilic phase.

6. The topical product according to claim 1, wherein the amino acids present in the hydrophilic phase are selected from glycine, proline, hydroxy-proline, arginine and lysine and the vitamins are riboflavin and vitamin C.

7. The topical product according to claim 6, wherein the amino acids have a final concentration by weight of 0.01% to 12%, and the vitamins have a final concentration by weight of 0.05% to 2%, all final concentrations based on the weight of the hydrophilic phase.

8. The topical product according to claim 7, wherein the amino acids have a final concentration by weight of 0.02% to 10%, and the vitamins have a final concentration by weight of 0.06% to 1.5%, all final concentrations based on the weight of the hydrophilic phase.

9. The topical product according to claim 8, wherein the amino acids have a final concentration by weight of 0.03% to 10%, and the vitamins have a final concentration by weight of 0.07% to 1%, all final concentrations based on the weight of the hydrophilic phase.

10. The topical product according to claim 1, wherein the tartaric acid is present at a final concentration by weight of 3% to 12%, the citric acid is present at a final concentration by weight of 0.4% to 4%, the salicylic acid is present at a final concentration by weight of 0.75% to 12%, the lactobionic acid is present at a final concentration by weight of 4% to 10%, and trichloroacetic acid has a final concentration by weight of 7% to 55%, all final concentrations based on the weight of the hydrophilic phase.

11. The topical product according to claim 1, wherein the tartaric acid is present at a final concentration by weight of 4% to 10%, the citric acid is present at a final concentration by weight of 0.5% to 3%, the salicylic acid is present at a final concentration by weight of 1% to 10%, the lactobionic acid is present at a final concentration by weight of 5% to 11%, and trichloroacetic acid has a final concentration by weight of 9% to 50%, all final concentrations based on the weight of the hydrophilic phase.

12. The topical product according to claim 1, wherein the hydrophilic phase further comprises additives, preservatives, pH adjusters, wetting agents, and rheological modifiers selected from viscosifying and gelling agents.

13. The topical product according to claim 1, wherein the hydrophilic phase further comprises cationic polymers, silica, ethylenediaminetetraacetic acid (EDTA), potassium hydrogen phosphate, glycerol, wetting agents and sodium hydroxide.

14. The topical product according to claim 1, wherein the lipophilic phase of the topical product further comprises isopropyl-myristate is at a final concentration of 30% to 75%, and petrolatum oil in a final concentration of 20% to 50%, all final concentrations based on the weight of the lipophilic phase.

15. The topical product according to claim 14, wherein isopropyl-myristate is at a final concentration of 40% to 70%, and petrolatum oil is at final concentration of 25% to 45%, all final concentrations based on the weight of the lipophilic phase.

* * * * *